Figure 1A:
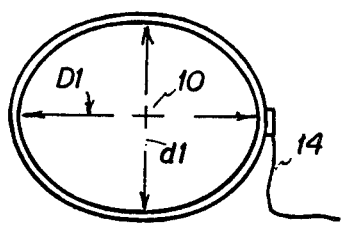

United States Patent

Kraus

[11] 4,066,065
[45] Jan. 3, 1978

[54] COIL STRUCTURE FOR ELECTROMAGNETIC THERAPY

[76] Inventor: Werner Kraus, Kaulbachstrasse 71, 8000 Munich 22, Germany

[21] Appl. No.: 689,376

[22] Filed: May 24, 1976

[51] Int. Cl.² ............................................. A61N 1/42
[52] U.S. Cl. .................................. 128/1.5; 128/82.1; 128/419 F; 219/10.79; 336/225
[58] Field of Search ................................ 128/1.3–1.5, 128/82.1, 404, 405, 411, 419 F; 219/10.79; 336/225

[56] References Cited

U.S. PATENT DOCUMENTS

| 96,044 | 10/1869 | Smith | 128/1.5 |
| 1,394,810 | 10/1921 | Craddick | 128/1.5 |
| 3,890,953 | 6/1975 | Kraus et al. | 128/1.5 |
| 3,915,151 | 10/1975 | Kraus | 128/1.5 |

FOREIGN PATENT DOCUMENTS 584,007   10/1958   Italy .................................. 128/1.3

OTHER PUBLICATIONS

Bennett, "Magnetism", 1906, pp. 1-30.

Primary Examiner—Dalton L. Truluck
Assistant Examiner—Lee S. Cohen
Attorney, Agent, or Firm—Flynn & Frishauf

[57] ABSTRACT

At least one layer of windings is so arranged to enclose an open space for treatment of a portion of a patient, for example the thorax, or a limb, shaped so that it encloses an open space which is elliptical or oval. The space enclosed thus is an oval or elliptical cylinder and, in a form suitable for treatment of the hip joint, can be an inclined cylinder. The winding is surrounded by a protective layer, for example a polyester resin which additionally can be shaped to provide for a support surface.

8 Claims, 4 Drawing Figures

COIL STRUCTURE FOR ELECTROMAGNETIC THERAPY

Cross reference to related patents: U.S. Pat. Nos. 3,745,995, by the inventor hereof, and 3,890,953, by the inventor hereof jointly with Hans-Dieter Viehbach.

The present invention relates to a coil structure for electromagnetic therapy having one or more windings surrounding an open space, the windings being adapted for connection to an electric generator, to form an electromagnetic therapy apparatus for treatment of a portion of the body or a limb of a patient by a low-frequency magnetic field located in the space surrounded by the winding or windings of the coil structure.

An electromagnetic therapy apparatus has previously been described in U.S. Pat. No. 3,890,953, by the inventor hereof jointly with Hans-Dieter Viehbach, in which a generator is provided to generate a low-frequency alternating current, connected to a coil which generates a corresponding low-frequency magnetic field. The magnetic field can be used directly for treatment of the patient's body or limbs, or to induce low-frequency alternating currents in a pick-up coil which forms the device to favor bone growth, or the like, as described in detail in applicant's prior U.S. Pat. No. 3,745,995. The disclosures of these patents are hereby incorporated by reference.

The coil which surrounds a space to receive the limb or body portion of the patient, as proposed in the prior patents, is formed with an essentially circular or U-shaped open cross section. It has been found that the field concentration to be obtained can be improved by deviating from this shape, while simultaneously increasing the ease of application and the comfort of the patient.

It is an object of the present invention to improve the coil structure for use in electromagnetic, or similar therapy by providing a better generated field or treatment field with better field distribution and which has improved characteristics relating to comfort and application as far as the wearer or patient is concerned.

SUBJECT MATTER OF THE PRESENT INVENTION

Briefly, the coil structure is so arranged that it encloses a space therein which has essentially oval or elliptical cross section. In accordance with a feature of the invention, the coil essentially has the shape of the surface of an inclined elliptical cylinder.

The coils in accordance with the present invention have particularly good adaptability to the human body. Their use and wear are not found to be essentially impeding while, at the same time, they ensure high-field concentration in the limb or body portion of the patient who is to be treated. The embodiment which uses an inclined elliptical cylinder is particularly suitable to generate fields in the region of the human hip joint.

Figure 2A:
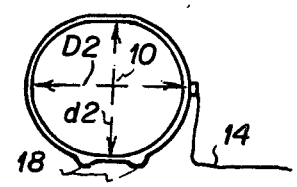
Figure 1B:
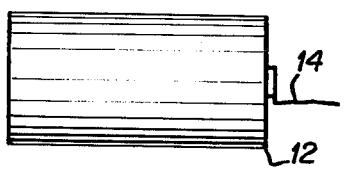
Figure 2B:
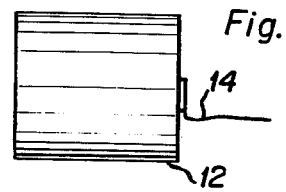
Figure 3:
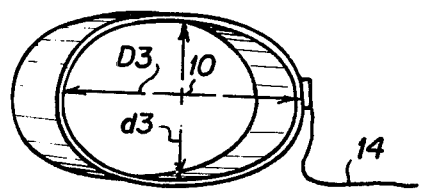
Figure 4:
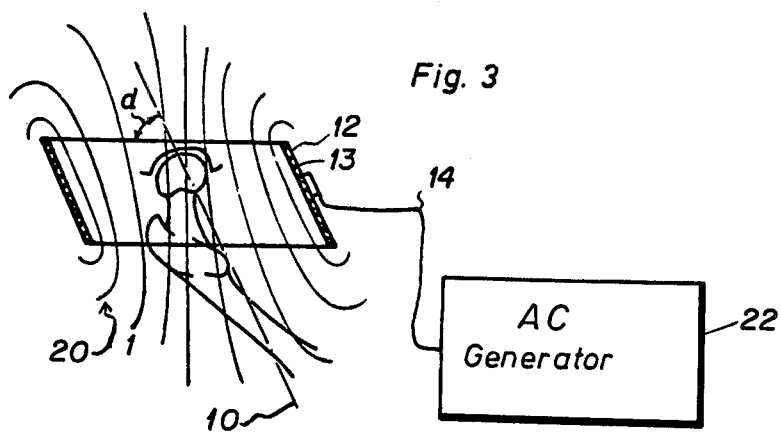

The invention will be described by way of example with reference to the accompanying drawings, wherein:

FIG. 1, in views (a) and (b) shows, respectively, a side view and a top view of the coil which is particularly suitable for treatment of the human thorax or the pelvis;

FIG. 2, in views (a) and (b) shows, respectively, a side view and a top view of another embodiment of the invention which is particularly suitable for treatment of a limb of the human body, for example the upper thigh;

FIG. 3 is a perspective side view of another embodiment illustrating an inclined elliptical cylinder, particularly suitable for treatment of the region of the hip joint of the human body; and FIG. 4 is a part sectional, part schematic view of the embodiment of FIG. 3, and showing the entire system.

The coil structure illustrated in FIG. 1 is a straight elliptical cylinder; the planes of the facing surfaces of the cylindrical jacket of the cylinder are perpendicular to the axis 10 thereof. Windings 12, seen schematically only in FIG. 1, and of which four layers are illustrated, enclose a generally elliptical shape; the windings 12 are embedded in a surrounding filler or jacket material 13, so that the coil structure has a smooth outer surface, the edges or corners of which are also rounded. the jacketing material may, for example, be a polyester resin with suitable fillers and pigments enclosed therein. The electrical conductors of the coil structure 12 are connected to a two-connecting line 14 which is connected to an a-c generator 22 (FIG. 4); for a specific description of the characteristics of the generator, reference is made to the aforementioned patents.

The dimensions of the ellipse enclosed by the coil of FIG. 1, when applied for example to the pelvis or thorax of a human body, may for example be in the order of about D1 : 41cm; d1 : 33½cm. A coil structure of this type fits particularly well to the human body and is not felt to be bothersome; it has good mechanical strength and provides an effective field concentration. The field generated extends generally parallel to the direction of the main blood vessels; the field is essentially longitudinal.

The embodiment of FIG. 2 is similar to that of FIG. 1 but the dimensions are somewhat smaller; D2 may, for example, be about in the order of 25cm and d2 in the order of about 22cm. This structure, which has the shape of a compressed or flattened oval, is particularly suitable for the limbs, that is, arms or legs of a patient. The windings of the coil, of which three are shown, are embedded in a jacketing mass which is formed with a support surface having two slightly projecting longitudinal ridges 18 which form support legs, to permit reliable positioning of the coil on a table, on a treatment chair, or cart, or the like.

The embodiment of FIGS. 3 and 4 is shaped as a relatively short, inclined, elliptical cylinder, that is, the end faces of the coil structure, in cross section, are ellipses of essentially the same size and shape, in parallel planes which, however, are angled with respect to the central axis 10 by an angle $\alpha$ differing from 90°. A suitable angle is, for example, in the order of about 27°; this angle is not critical and may vary widely depending on desired use. The embodiment of FIGS. 3 and 4 is particularly suitable for treatment of the human body in the region of the hip joint; the field lines 20 of the resulting magnetic field extend, essentially, in longitudinal direction, as best seen in FIG. 4, and have a major vector direction along the neck of the femur as is clearly seen in FIG. 4. The windings 12 are surrounded by a jacket 13 of polyester, for example by being cast therein. The outer surface, as well as the inner surface of the coil are smooth and the edges are rounded. A-C generator 22 supplies a low-frequency a-c to the coil 12 through line 14.

The a-c generator has an output which is so matched to the number of turns of the coil and the surface surrounded thereby that is provides a low-frequency field in the order of from about 5 to 30 Hz of about 35 to 50

Gauss. None of these values are critical; a field strength of 100 Gauss or more can be generated. The dimension D3 of the coil of FIGS. 3 and 4 may be in the order of about 40 cm; the dimension d3 in the order of about 24–25cm.

Various changes and modifications may be made and the dimensions can be suitably arranged to fit users of various sizes.

I claim:

1. Coil structure for electromagnetic therapy comprising at least one layer of electrically conductive windings (12) and terminal means (14) connected to the windings to connect the windings to a source (22) of alternating current, said windings enclosing an open space for treatment of a portion of the body of a patient by generating a low-frequency electromagnetic field upon connection of the windings to said source (22), wherein said windings are shaped to form an elliptical cylinder the end faces of said cylinder being inclined with respect to the central axis of said cylinder, such that the space enclosed thereby is oval, or essentially elliptical in cross section.

2. Structure according to claim 1, wherein a jacketing mass (13) is provided, the windings (12) being embedded in the jacketing mass, the jacketing mass providing a smooth surface and having rounded edges.

3. Structure according to claim 2, wherein the jacketing mass is formed with a ridged support surface (18).

4. Structure according to claim 1, wherein the end faces formed by the windings of the inclined elliptical cylinder are in parallel planes.

5. Structure according to claim 4, wherein the angle ($\alpha$) of inclination of the end faces with respect to the central axis is in the order of about 27°.

6. Structure according to claim 1, wherein the angle ($\alpha$) of inclination of the end faces with respect to the central axis is in the order of about 27°.

7. Coil structure according to claim 1 adapted for treatment of the human hip joint
wherein the coil dimension of the oval or essentially elliptical cross-sectional space enclosed by the coil has a larger diametrical dimension (D3) in the order of about 40cm and a smaller diametrical dimension (d3) in the order of about 25cm.

8. Coil structure according to claim 7, wherein the end faces of the cylinder formed by the windings are in essentially parallel planes, and the angle ($\alpha$) of inclination of the end faces with respect to the central axis is in the order of about 27°.

* * * * *